(12) United States Patent
Kozel et al.

(10) Patent No.: US 11,560,535 B2
(45) Date of Patent: Jan. 24, 2023

(54) ORGANIC PEROXIDE DISPERSIONS

(71) Applicant: Arkema Inc., King of Prussia, PA (US)

(72) Inventors: Thomas H. Kozel, Pottstown, PA (US); Lisa B. Rachwal, Harleysville, PA (US)

(73) Assignee: Arkema Inc., King of Prussia, PA (US)

( * ) Notice: Subject to any disclaimer, the term of this patent is extended or adjusted under 35 U.S.C. 154(b) by 0 days.

(21) Appl. No.: 16/307,158

(22) PCT Filed: Jun. 6, 2017

(86) PCT No.: PCT/US2017/036112
§ 371 (c)(1),
(2) Date: Dec. 5, 2018

(87) PCT Pub. No.: WO2017/214115
PCT Pub. Date: Dec. 14, 2017

(65) Prior Publication Data
US 2019/0292495 A1    Sep. 26, 2019

Related U.S. Application Data

(60) Provisional application No. 62/347,674, filed on Jun. 9, 2016.

(51) Int. Cl.
| | |
|---|---|
| *A61K 8/38* | (2006.01) |
| *C11D 3/395* | (2006.01) |
| *A61K 8/02* | (2006.01) |
| *A61K 8/04* | (2006.01) |
| *A61K 8/365* | (2006.01) |
| *A61K 8/39* | (2006.01) |
| *A61Q 19/00* | (2006.01) |
| *C11D 1/74* | (2006.01) |
| *C11D 3/20* | (2006.01) |
| *C11D 17/00* | (2006.01) |
| *C08K 5/098* | (2006.01) |
| *C08K 5/14* | (2006.01) |
| *C07C 407/00* | (2006.01) |
| *C11D 3/39* | (2006.01) |

(52) U.S. Cl.
CPC .......... *C11D 3/3951* (2013.01); *A61K 8/0241* (2013.01); *A61K 8/042* (2013.01); *A61K 8/044* (2013.01); *A61K 8/365* (2013.01); *A61K 8/38* (2013.01); *A61K 8/39* (2013.01); *A61Q 19/00* (2013.01); *C07C 407/006* (2013.01); *C08K 5/098* (2013.01); *C08K 5/14* (2013.01); *C11D 1/74* (2013.01); *C11D 3/2075* (2013.01); *C11D 3/2086* (2013.01); *C11D 3/3947* (2013.01); *C11D 17/0013* (2013.01); *A61K 2800/10* (2013.01)

(58) Field of Classification Search
CPC ...... A61K 8/0241; A61K 8/042; A61K 8/044; A61K 8/365; A61K 8/38; A61K 8/39; A61K 2800/10; C11D 3/395; C11D 3/3951; C11D 3/2075; C11D 3/2086; C11D 3/3947; C11D 3/222; C11D 3/3945; C11D 1/74; C11D 1/667; C11D 17/0013; A61Q 19/00; C07C 407/006; C07C 409/04; C07C 409/06; C07C 409/30; C08K 5/098; C08K 5/14

See application file for complete search history.

(56) References Cited

U.S. PATENT DOCUMENTS

| | | | |
|---|---|---|---|
| 2,208,417 | A | 7/1940 | Penn |
| 2,272,576 | A | 2/1942 | Penn |
| 2,272,577 | A | 2/1942 | Penn |
| 2,347,434 | A | 4/1944 | Reichert et al. |
| 2,453,070 | A | 11/1948 | Hyatt et al. |
| 3,324,040 | A | 6/1967 | Spoor |
| 3,591,540 | A | 7/1971 | Praskach |
| 3,795,630 | A | 3/1974 | Jasper et al. |
| 4,056,611 | A | 11/1977 | Young |
| 4,387,107 | A * | 6/1983 | Klein ...................... A61K 8/38 514/714 |
| 4,515,929 | A | 5/1985 | Tang |
| 4,734,135 | A | 3/1988 | Satomi et al. |
| 4,917,816 | A | 4/1990 | Self |
| 5,057,479 | A | 10/1991 | Bock |
| 5,110,495 | A | 5/1992 | Self |
| 5,300,600 | A | 4/1994 | Bock et al. |
| 5,690,856 | A | 11/1997 | Milleville et al. |
| 6,433,024 | B1 | 8/2002 | Popp et al. |
| 8,263,097 | B2 * | 9/2012 | Jitpraphai ............... A61P 17/10 424/402 |
| 8,697,130 | B1 * | 4/2014 | Gerlach ................... A61K 8/38 424/489 |
| 9,217,044 | B2 | 12/2015 | Gravelle et al. |
| 2006/0019936 | A1 * | 1/2006 | Eissigmann ......... A61K 31/573 514/179 |

(Continued)

FOREIGN PATENT DOCUMENTS

| | | |
|---|---|---|
| EP | 0 737 474 A2 | 10/1996 |
| WO | WO 82/00104 | 1/1982 |

(Continued)

OTHER PUBLICATIONS

Zhong et al., Rheological behavior of xanthan gum solution related to shear thinning fluid delivery for subsurface remediation, Nov. 21, 2012, Journal of Hazardous Materials, vol. 244-245, pp. 160-170. (Year: 2012).*

*Primary Examiner* — Ali Soroush

(74) *Attorney, Agent, or Firm* — Lynn B. Morreale

(57) ABSTRACT

Evaporation of water from an aqueous dispersion of a solid peroxide such as benzoyl peroxide is retarded by the incorporation of carboxylic acid salt. The carboxylic acid salt renders the aqueous dispersion less susceptible to explosive decomposition when exposed to external triggering events such as impact, heat, friction or contamination, yet does not interfere with the ability to achieve and maintain a stable, small particle size dispersion having desirable viscosity and flow properties.

13 Claims, 2 Drawing Sheets

(56) References Cited

U.S. PATENT DOCUMENTS

| | | | |
|---|---|---|---|
| 2011/0212157 A1 | 9/2011 | Edelson et al. | |
| 2013/0252869 A1* | 9/2013 | Oh | C11D 11/0017 510/155 |
| 2013/0323228 A1 | 12/2013 | Norman | |
| 2013/0344152 A1* | 12/2013 | Kozel | A61K 47/08 424/489 |
| 2014/0161853 A1 | 6/2014 | Gerlach et al. | |
| 2015/0165043 A1 | 6/2015 | Kozel et al. | |

FOREIGN PATENT DOCUMENTS

| | | | | |
|---|---|---|---|---|
| WO | WO-03000787 A1 * | 1/2003 | | A61K 8/0212 |
| WO | WO 2013/187949 A1 | 12/2013 | | |

* cited by examiner

ORGANIC PEROXIDE DISPERSIONS

This application is a national stage application under 35 U.S.C. § 371 of PCT/US2017/036112 filed Jun. 6, 2017, which claims benefit to U.S. patent application Ser. No. 62/347,674, filed Jun. 9, 2016.

FIELD OF THE INVENTION

The invention pertains to aqueous dispersions of water-insoluble solid organic peroxides, uses for such dispersions and methods of making such dispersions.

DISCUSSION OF THE RELATED ART

Peroxides generally have a tendency to be flammable and explosive, with some peroxides exhibiting such properties to a greater extent than others. For example, benzoyl peroxide may decompose when dry due to shock, friction or static electricity. This property carries with it the hazards to the users of these materials as well as to the manufacturers and intermediate handlers thereof. Accordingly, it has long been an object to provide flame resistant organic peroxide compositions.

In recent years, technology has been developed which makes possible the production of aqueous dispersions of normally solid organic peroxides. Such dispersions are typically pastes or liquids containing high concentrations of the peroxide, wherein the peroxide is present in the form of small particles (e.g., less than 10 μm diameter, on average). The pastes are shear thinning or sufficiently flowable so as to be pumpable, pourable and/or sprayable, which makes their handling and use easier. Dispersions of this type are described, for example, in US 2013/0344152 and US 2015/0165043.

However, known aqueous dispersions of benzoyl peroxide have the disadvantage that the water present in the dispersion may tend to evaporate under certain conditions, leaving a dry, highly concentrated benzoyl peroxide residue. Such a residue is susceptible to undergoing explosive decomposition when exposed to such external triggering events as impact, friction, heat and/or contamination. It would therefore be desirable to develop methods and formulations wherein evaporation of the water is suppressed or hindered. However, such improvements are challenging to achieve. The present inventors have found that the introduction of many substances having the intended purpose of retarding water loss is not sufficiently effective and/or detrimentally affects or interferes with other attributes of the aqueous dispersions such as viscosity or dispersion stability.

SUMMARY OF THE INVENTION

It has now been discovered that the incorporation of salts of carboxylic acids, wherein the salt preferably includes a monovalent cation such as potassium or sodium, into aqueous dispersions of water-insoluble, solid organic peroxides such as benzoyl peroxide is unexpectedly effective in suppressing the rate at which water evaporates from the dispersion, yet does not interfere with the ability to produce stable, shear thinning/flowable dispersions of small (e.g., <10 μm) particle size, high concentration organic peroxide formulations. Such salts may further function as phlegmatizers and help to safeguard the aqueous dispersions, making them less susceptible to detonation or other types of uncontrolled decomposition and thus more stable and safer to handle, transport and use.

DETAILED DESCRIPTION OF CERTAIN EMBODIMENTS OF THE INVENTION

Figure 1:
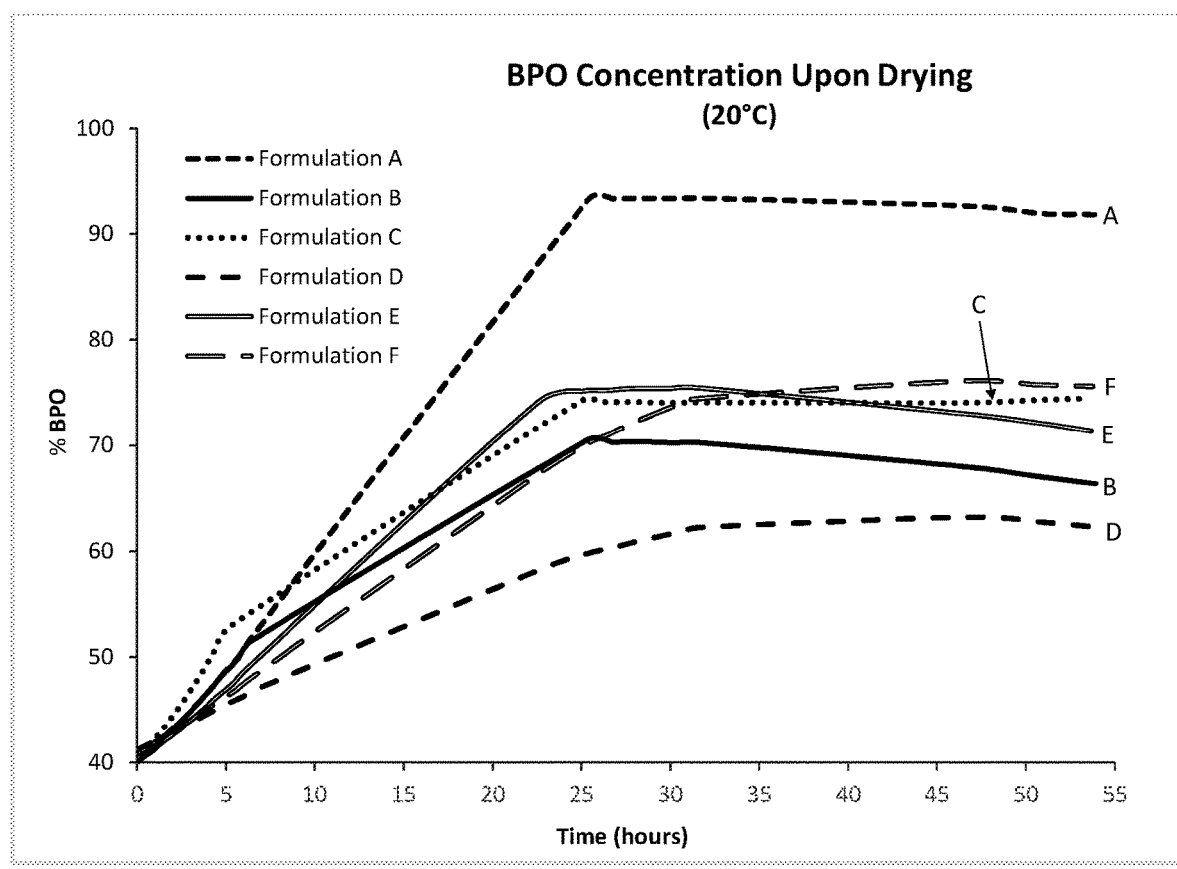
FIGS. 1 and 2 show experimental results obtained in Example 1.

Aqueous dispersions of the present invention comprise an organic peroxide which is normally solid (i.e., a solid at 25° C.).

Examples of preferred suitable organic peroxides include ketone peroxides, such as 1-hydroxy cyclohexyl peroxide and 1-hydroperoxycyclohexyl peroxide; aldehyde peroxides such as 1-hydroxy heptyl peroxide; peroxy dicarbonates such as dicetyl peroxydicarbonate, di(4-t-butylcyclohexyl) peroxydicarbonate, dicyclohexyl peroxydicarbonate and dimyristal peroxydicarbonate; acylperoxy alkylcarbonates, such as acetyl peroxy stearyl carbonate and the like and mixtures thereof.

Examples of more preferred suitable organic peroxides include aliphatic diacyl peroxides, such as decanoyl peroxide, lauroyl peroxide and myristoyl peroxide.

Examples of most preferred suitable organic peroxides include aromatic diacyl peroxides, such as benzoyl peroxide, o-methylbenzoyl peroxide, o-methoxybenzoyl peroxide, o-ethoxy benzoyl peroxide, o-chlorobenzoyl peroxide and 2,4-dichlorobenzoyl peroxide; and peroxyesters, such as t-butylperoxy maleic acid. In one particularly advantageous embodiment, benzoyl peroxide is the organic peroxide.

Other organic peroxides which are normally solid at room temperature and substantially insoluble in water may also be employed. The starting organic peroxide may be obtained by any suitable method and may be in solid (dry) form or in the form of a mixture with water. As will be described in more detail hereafter, the organic peroxide may have a relatively large particle size to begin with (e.g., greater than 10 μm) and then is reduced in size through any suitable procedure in the presence of a surfactant and water to provide an aqueous dispersion.

The present aqueous dispersions may comprise about 30 percent or more or about 35 percent or more by weight of an organic peroxide. One of the features of the present invention is that it enables the preparation of aqueous dispersions containing relatively high concentrations of organic peroxide, wherein the dispersions are pumpable or pourable because they are shear thinning or flowable liquids. In this description, shear thinning means that viscosity drops as the shear rate increases. Thus, the viscosity of the peroxide dispersions in at least certain embodiments of the present invention will drop as the dispersion is stirred or mixed and it becomes pourable or pumpable, thereby easing use. In some embodiments of the invention, the aqueous dispersion is sufficiently fluid such that it is capable of being poured even without being subjected to stirring or mixing. The concentration of the peroxide in the aqueous dispersion may be adjusted as may be desired or needed, but typically the organic peroxide concentration is at least about 30 weight percent but not greater than about 75 weight percent, or between about 35 to 60 weight percent, or between about 37 to not greater than about 53 weight percent, or between about 37 to about 42 weight percent.

Sufficient water is present in admixture with the organic peroxide to provide an aqueous dispersion, with water acting as a liquid matrix within which particles of the organic peroxide are dispersed. Typically, the water content of the aqueous dispersion is from about 25 to 70 weight percent, from about 40 to 65 weight percent, from about 42 to about 60 weight percent, or from about 45 to about 55 weight percent, from about 48 weight percent to about 53 weight percent. The pH of the water may be adjusted as may be desired or needed by the addition of one or more pH adjusting agents such as bases, acids, buffers and the like. Soluble species such as salts may also be present. The aqueous phase of the dispersion should, however, be basic. Thus, the pH of the aqueous phase is greater than 7. In various embodiments, the aqueous phase pH is from 7.5 to 10 or from 8 to 9. If the desired aqueous phase pH is not achieved as a result of the characteristics of the other components of the dispersion, a basic pH may be attained by the addition of an effective amount of one or more bases.

Suitable bases include organic as well as inorganic bases; the base may be a strong and/or weak base. For example, ammonium, alkali metal and alkaline earth hydroxides and phosphates may be used. Examples of preferred suitable bases include calcium hydroxide, magnesium hydroxide, and potassium phosphates (mono and dibasic salts). Ammonium hydroxide is an example of a more preferred suitable base. Examples of bases that are most preferred include sodium hydroxide and potassium hydroxide.

One or more buffering agents may be present in order to help maintain the pH of the aqueous phase within a desired range or at a desired value. Examples of preferred suitable buffers include citrate buffer systems (e.g., sodium or potassium citrate) and phosphate buffer systems. Examples of more preferred suitable buffers include sodium carbonate, potassium carbonate, calcium carbonate, magnesium carbonate, calcium bicarbonate, and magnesium bicarbonate. Sodium bicarbonate and potassium bicarbonate are examples of most preferred buffers.

In various embodiments, the aqueous dispersion is formulated using 0.1 to 3 weight % or about 0.25 to 1 weight % base and/or buffer.

Besides water and organic peroxide, the aqueous dispersions of the present invention also comprise one or more surfactants. In one embodiment, the surfactant is a pharmaceutically acceptable surfactant. A pharmaceutically acceptable surfactant refers to a surfactant that does not cause significant irritation to an organism and does not abrogate the biological activity and properties of an administered compound that the dispersion of the present invention is combined with. In another embodiment, the surfactant is a food grade surfactant. A food grade surfactant refers to a surfactant which is permitted by regulation to be present in a foodstuff, at least up to certain levels. The surfactant used may be both a pharmaceutically acceptable surfactant and a food grade surfactant.

The surfactant may be any surface active agent or combination of surface active agents capable of imparting the desired degree of stability to the aqueous organic peroxide dispersion. The surfactant thus functions to help keep the organic peroxide particles stably dispersed in the aqueous phase. Suitable surfactants include those selected from the group consisting of anionic surfactants, nonionic surfactants, amphoteric surfactants and combinations thereof, with nonionic surfactants being utilized in one advantageous embodiment of the invention.

Polyglyceryl esters of one or more C6-C18 fatty acids, or preferably polyglyceryl esters of one or more C6-C12 fatty acids, or preferably polyglyceryl esters of one or more C8-C12 fatty acids, are surfactants which are particularly effective in providing dispersions which remain free flowing liquids during the milling process which may be used to reduce the average particle size of the organic peroxide to below 10 μm and preferably above 2 μm. That is, the use of other types of surfactants may lead to the formation of very thick pastes during milling that significantly increases the time needed to achieve a particular desired small particle size.

Polyglyceryl esters of fatty acids are also referred to in the art as "polyglycerol esters of fatty acids" and "polyglycerol fatty acid esters." They may be described as mixed partial esters formed by reacting polymerized glycerols with edible fats, oil or fatty acids. Commercial surfactants which are polyglyceryl esters of fatty acids may include minor amounts of mono-, di- and tri-glycerides, free glycerol and polyglycerols, free fatty acids and/or salts of free fatty acids. The degree of polymerization of the polyglyceryl component may vary. In various embodiments of the present invention, the polyglyceryl segment of the surfactant may contain at least 2, 3, 4, 5, 6, 7, 8 or 9 and/or not more than 20, 19, 18, 17, 16, 15, 14, 13, 12 or 11 glyceryl repeating units on average per molecule. In one particular embodiment, about 10 glyceryl repeating units per molecule on average are present.

The use of polyglyceryls esterified with relatively short chain fatty acids as surfactants in a process wherein a relatively large particle size organic peroxide (e.g., having an average particle size greater than 10 μm) is milled in water to a smaller particle size (e.g., less than 10 μm or less than 5 μm average particle size and in some embodiments preferably greater than 2 μm average particle size) helps to lower viscosity during such a milling process. The resulting aqueous dispersion is shear thinning. The fatty acids used to esterify the polyglyceryl thus are predominantly C6-C18 fatty acids, or C6-C12 fatty acids, or C8-C12 fatty acids (i.e., fatty acids containing 6 to 18, or 6 to 12, or 8 to 12 carbon atoms per molecule), although minor amounts of shorter and/or longer chain fatty acids may also be present in the esterified polyglyceryl. For example, in various embodiments of the invention, at least 50, at least 60, at least 70, at least 80, at least 90 or essentially all of the fatty acid moieties present in the surfactant are C6-C18 or C6-C12 fatty acid moieties. Mixtures of different C6-C18, C6-12, or C8-C12 fatty acid moieties may be present. The fatty acid moieties may be straight chain or branched, saturated or unsaturated. Typically, the fatty acid moieties are monocarboxylate moieties corresponding to the general structure —OC(=O)R, where R is a C5-C11 alkyl group. In one embodiment, the fatty acid moieties present in the surfactant are predominantly saturated, such that the iodine value of the surfactant is less than 10 or less than 5. Examples of suitable C6-C18 fatty acids include, but are not limited to, hexanoic acid (also known as caproic acid), octanoic acid (also known as caprylic acid), decanoic acid (also known as capric acid) and dodecanoic acid (also known as lauric acid), tetradecanoic acid (also known as myristic acid) hexadecanoic acid (also known palmitic), octadecanoic (also known as steraric acid) and mixtures thereof. In one embodiment, the C6-C12 fatty acid is a mixture of octanoic acid and decanoic acid (with other fatty acids possibly being present in minor amounts).

Typically, the polyglyceryl is partially esterified with fatty acid moieties, with one or more hydroxyl groups remaining unesterified. For example, the surfactant may contain an average of 1 to 3 fatty acid moieties per molecule. In certain embodiments, from about 25% to about 60%, or from about 30% to about 50%, of the available hydroxyl groups in the polyglyceryl are esterified with fatty acid moieties.

The surfactant may correspond to the general structure (I):

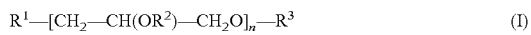  (I)

wherein the average value of n is from about 6 to about 14 and $R^1$, $R^2$ and $R^3$ are each independently a C6-C18 fatty acid moiety or hydrogen, provided that at least one of $R^1$, $R^2$ or $R^3$ is a C6-C18 fatty acid moiety. In one embodiment, at least one, but not more than two, of $R^1$, $R^2$ or $R^3$ is hydrogen. Although structure (I) shows the glyceryl repeating units arranged in a linear fashion, it is understood that the formula also encompasses polyglyceryls which are branched.

Exemplary surfactants useful in the present invention include, but are not limited to, polyglyceryl-10 caprylate/caprate, polyglyceryl-10 caprylate, polyglyceryl-10 caprate, polyglyceryl-10 laurate, as well as analogous substances where the polyglyceryl component contains an average of 8, 9, 11 or 12 glycerol repeating units per molecule. Polyglyceryl esters of C6-C18 fatty acids and polyglyceryl esters of C6-C12 fatty acids suitable for use as surfactants in the present invention are available commercially from various suppliers.

In various aspects of the invention, the surfactant may have an HLB value of at least 12, 13, or 14 and/or an HLB value of not more than 18, 17 or 16. For example, the HLB value of the surfactant may be 12-18 or 14-16.

In one embodiment of the invention, the only type of surfactant present in the aqueous dispersion is a polyglyceryl ester of C6-C18 or C6-C12 fatty acids or a mixture of such surfactants. In other embodiments, such polyglyceryl esters represent at least 50, 60, 70, 80, 90 or 95% by weight of the total amount of surfactant present.

Surfactant may be combined with water and the organic peroxide in an amount effective to reduce the viscosity of the aqueous dispersion during milling of the organic peroxide. Typically, the concentration of surfactant in the aqueous dispersion is at least 0.1 weight % but no greater than 2.0 weight %.

To assist in maintaining the product as a stable, homogeneous dispersion and inhibit settling out of the particles of organic peroxide, one or more gelling agents may be incorporated in the aqueous dispersion. A gelling agent is a substance capable of forming a gel when placed in water. Macromolecular gelling agents are particularly useful in the present invention, especially macromolecular gelling agents of natural origin such as certain polysaccharides. Suitable macromolecular gelling agents include, but are not limited to, alginates (salts of alginic acid), carrageenans, gellan gum, guar gum pectic substances (e.g., pectic acid, pectin, pectate), cellulose gum, microcrystalline cellulose and xanthan gum. The gelling agent may be selected such that it is suitable for inclusion in a food or pharmaceutical product. In one embodiment, the gelling agent forms a gel when placed in water without the need to combine the gelling agent with a crosslinking agent. In another embodiment, the gelling agent is capable of being further gelled through crosslinking. For example, a macromolecular gelling agent may contain one or more different types of functional groups along its backbone or pendent to the backbone which are capable of interacting or reacting with a crosslinking agent. Such functional groups may be carboxylic acid groups, sulfonic acid groups or salts thereof (carboxylates, sulfates), for example. Suitable crosslinking agents may include species providing polyvalent cations (e.g., divalent and trivalent cations). Exemplary polyvalent cations include aluminum, barium, calcium, copper, iron, magnesium, strontium, and zinc cations. The cations may be supplied in the form of food-safe and/or pharmaceutical-safe salts. Specific examples of suitable salts useful as crosslinking agents include the following, including their hydrates, and mixtures thereof: calcium carbonate, calcium chloride, calcium disodium edetate, calcium hydroxide, calcium lactate, calcium nitrate, calcium oxalate, calcium oxide, calcium sulfate, dicalcium phosphate, tricalcium citrate, tricalcium phosphate, and the corresponding barium, copper, iron, magnesium, strontium, and zinc analogues thereof. The amounts of macromolecular gelling agent and crosslinking agent may be varied as desired. The gelling agent may be utilized in an amount effective to reduce the tendency of the particulate organic peroxide to settle out of the aqueous dispersion over time.

In various embodiments, the aqueous dispersion contains at least 0.15 weight % or at least 0.4 weight % gelling agent (e.g., macromolecular gelling agent). In other embodiments, the aqueous dispersion contains not more than 1.5 weight % or not more than 0.75 weight % gelling agent. For example, the aqueous dispersion may comprise 0.25 to 1.5 weight % macromolecular gelling agent. The amount of crosslinking agent, if used, may generally be varied in accordance with how much macromolecular gelling agent is present. For example, if the concentration of macromolecular gelling agent is relatively low, the concentration of crosslinking agent may also be relatively low. Typical concentrations of crosslinking agent may be, for example, from 0.01 to 1 weight %.

The aqueous dispersions of the present invention are further characterized by the inclusion of at least one carboxylic acid salt. Carboxylic acid salt is present in an amount effective to reduce water evaporation and/or the rate at which water evaporates from the aqueous dispersion, which generally is an amount of about 2% or more of the total weight of the aqueous dispersion. For example, the aqueous dispersion may comprise at least 2% by weight, at least 3% by weight or at least 4% by weight of such carboxylic acid salt. Typically, the amount of carboxylic acid salt in the aqueous dispersion does not exceed 15% by weight, 14% by weight, 13% by weight or 12% by weight.

Preferably, the cation portion of the carboxylic acid salt should be selected to be a monovalent cation such as an alkali metal cation (e.g., sodium or potassium cation). That is, in preferred embodiments of the invention the aqueous dispersion is comprised of at least one carboxylic acid salt comprising a monovalent cation. In certain embodiments, the carboxylic acid salt contains only monovalent cations (i.e., the only type of cation present in the carboxylic acid salt is monovalent cation). The use of carboxylic acid salts comprising polyvalent cations (e.g., Ca cation, Mg cation) may also be suitable, depending upon which gelling agent is chosen. Sodium is the preferred cation. In various embodiments, the carboxylate portion of the carboxylic acid salt is based on a relatively short chain carboxylic acid, such as a carboxylic acid containing 2, 3, 4, 5 or 6 carbon atoms. The carboxylic acid preferably is a monocarboxylic acid, i.e., a carboxylic acid containing a single carboxylic acid group per molecule. The carboxylic acid may contain one or more functional groups other than carboxylate, such as one or more hydroxyl groups. Thus, in certain embodiments, the carboxylic acid is a hydroxycarboxylic acid. Combinations of different carboxylic acid salts may be utilized. Illustrative examples of carboxylic acid salts suitable for use in the present invention include sodium lactate and potassium lactate.

In one embodiment, the carboxylic acid salt is a pharmaceutically acceptable carboxylic acid salt. A pharmaceutically acceptable carboxylic acid salt refers to a carboxylic acid salt that does not cause significant irritation to an organism and does not abrogate the biological activity and properties of an administered compound that the aqueous dispersion of the present invention is combined with. In another embodiment, the carboxylic acid salt is a food grade carboxylic acid salt. A food grade carboxylic acid salt refers to a carboxylic acid salt which is permitted by regulation to be present in a foodstuff, at least up to certain levels. The carboxylic acid salt used may be both a pharmaceutically acceptable carboxylic acid salt and a food grade carboxylic acid salt.

The aqueous dispersion may be prepared using any process wherein the aforementioned components are combined. For example, the aqueous dispersion may be prepared by milling/grinding an organic peroxide in the presence of water and surfactant until the desired particle size of the organic peroxide is achieved (e.g., less than 10 µm, or less than 5 µm, or between 3 to 5 µm, or 2 to 5 µm, or 1 to 5 µm, or between 3 to 10 µm, or 2 to 10 µm, or 1 to 10 µm). Particle size may be determined using ASTM UOP 856-07, Particle Size Distribution of Powder by Laser Light Scattering and is reported D50 by percent volume.

Milling or other mechanical means for reducing particle size may be carried out by any suitable equipment known in the art such as a rotor/stator mill, a horizontal ball mill, or, most preferably, a vertical basket mill. The temperature during milling should be controlled so as to avoid decomposition of the organic peroxide. Typically, the milling is conducted at temperatures of 40° C. or less. If a macromolecular gelling agent is to be included in the aqueous dispersion, it may be preferred to add it to the aqueous dispersion after the milling step. The aqueous dispersion also may be prepared using the methods known to those skilled in the art such as those disclosed in U.S. Pat. Nos. 4,039,475, 4,092,470, 4,734,135 and 4,440,885 and U.S. Patent Publication Nos. 2011/0086959, 2013/0344152 and 2015/0165043, the disclosures of which are incorporated herein in their entireties. Sonication and ultrasound applications/processes known in the art also are suitable.

Two exemplary and advantageous methods for preparing aqueous dispersions in accordance with the present invention may be described in detail as follows.

A first suitable method comprises the following steps:
a) mixing benzoyl peroxide (or other water-insoluble, solid organic peroxide) having an average particle size of about 10 µm or greater, surfactant, pH adjustment agent (e.g., base and/or buffer), and water to form a first pourable dispersion (wherein the aqueous phase of the dispersion is basic);
b) reducing the average particle size of the benzoyl peroxide in the first pourable dispersion to less than 10 µm (this may be done by mechanical means, e.g., by milling);
c) mixing the first pourable dispersion with a gelling agent, allowing sufficient time for the gelling agent to form a second pourable dispersion;
d) mixing the second pourable dispersion with at least one carboxylic acid salt to form a third pourable dispersion; and
e) optionally mixing the third pourable dispersion with at least one crosslinking agent capable of crosslinking the gelling agent step (if the gelling agent already contains a crosslinking agent, i.e., is already crosslinked, or does not require crosslinking with a crosslinking agent, this step is not needed). A pourable, pumpable and/or fluid composition is thereby obtained, which may be deposited in a container for storage and/or transport.

A second suitable method comprises the following steps:
a) mixing benzoyl peroxide having an average particle size of 10 µm or greater, surfactant, pH adjustment agent and water to form a first pourable dispersion;
b) reducing the average particle size of the benzoyl peroxide in the first pourable dispersion to less than 10 µm (for example, by mechanical means, e.g., milling);
c) mixing the first pourable dispersion with a pre-hydrated gelling agent (i.e., a gelling agent that has already been combined with a quantity of water) to form a second pourable dispersion;
d) mixing the second pourable dispersion with at least one salt of a carboxylic acid to form a third pourable dispersion; and
e) optionally mixing the third pourable dispersion with at least one crosslinking agent capable of crosslinking the gelling agent (if the pre-hydrated gelling agent has already been crosslinked with a crosslinking agent or does not require crosslinking with a crosslinking agent, this step is not needed). A pourable, pumpable and/or fluid composition is thereby obtained, which may be deposited in a container for storage and/or transport.

The components of aqueous dispersions of the present invention and the procedures used to prepare the aqueous dispersions are advantageously selected and controlled to allow for the pumpability and sprayability of the dispersions due to reduced particle size and low viscosity. The aqueous dispersions preferably have a viscosity at 25° C. of between 800-10,000 cps (centipoise), more preferably between 1,000-5,000 cps, and even more preferably between 1,000-2,000 cps determined using a Brookfield viscometer and ASTM D2196-10 (Standard Test Methods for Rheological Properties of Non-Newtonian Materials by Rotational (Brookfield Type) Viscometer. Such dispersions may be sprayed, for example, using pneumatic powered or even hand powered spray devices.

Aqueous dispersions in accordance with the present invention are useful in a wide variety of end use applications where it is desired to utilize organic peroxides, including the food industry as well as the pharmaceutical industry. For example, the aqueous dispersion may be used as a food bleach or as a component of an anti-acne medication. Use of aqueous dispersions in accordance with the present invention alleviate or avoid the problems typically associated with using organic peroxides in dry form, such as difficulties in readily dispersing the peroxide into a composition such as a food product, the generation of dust, and low efficiency in color removal.

In one embodiment, a method of decolorizing a product (e.g., reducing the color of a product, removing all color from a product, or bleaching a product) is provided, comprising contacting the product with an aqueous dispersion in accordance with the present invention. Products suitable for such treatment include food products as well as non-food industrial products. The food product may, for example, be selected from the group consisting of dairy products (e.g., whey, cheese, milk), edible oils, edible fats, polysaccharides (e.g., flour, starch), beverages (e.g., beer) and combinations thereof. Suitable non-food industrial products include, for example, non-edible oils and fats, paper (pulp), textiles and the like. The aqueous dispersion may be contacted with the product in an amount and for a time and at a temperature effective to reduce the color of the product. The conditions selected will depend upon the degree of color reduction desired or necessary as well as the type of product and organic peroxide, among other factors, but providing a solid organic peroxide in the aqueous dispersion having a small particle size (e.g., less than 10 μm on average) permits a given amount of color reduction to be achieved within a shorter period of time and/or using a lower amount or concentration of organic peroxide and/or under milder conditions (e.g., a lower contacting temperature) as compared to conventional organic peroxide dispersions or dry peroxide-containing compositions having larger particle sizes.

A pharmaceutical composition may be provided in accordance with the present invention which is comprised of an aqueous dispersion as described herein and at least one additional pharmaceutically acceptable ingredient. Any of the suitable pharmaceutically acceptable ingredients known in the art may be utilized, provided such ingredient is compatible with the organic peroxide. For example, one or more pharmaceutically active ingredients (e.g., antibacterial agents, antimicrobial agents) and/or excipients such as fillers, carriers, surfactants, pigments, stabilizers, rheology control agents, gelling agents and the like may be employed in combination with the aqueous dispersion of organic peroxide. The pharmaceutical composition may be an anti-acne medication and may be in the form of a lotion, soap, gel or cream, for example. Because of the small particle size of the organic peroxide and/or the opportunity to prepare higher concentration dispersions which are still pumpable or pourable, pharmaceutical compositions containing aqueous dispersions in accordance with the present invention may be formulated to be acting or more potent than conventional pharmaceutical compositions containing organic peroxide.

A personal care composition is provided in another embodiment of the invention wherein the personal care composition is comprised of an aqueous dispersion as described herein and at least one additional personal care ingredient. Any of the conventional personal care ingredients known in the art may be combined with the aqueous dispersion of organic peroxide such as, for example, carriers, fillers, surfactants, abrasives, rheology control agents, gelling agents, flavorants, remineralizers, emollients, bleach activators and the like and combinations thereof. The aqueous dispersions of the present invention may, for instance, be used as components of teeth whitening products (e.g., toothpastes, mouth rinses) and hair coloring or bleaching products.

In still another embodiment of the invention, a cleaning product comprised of an aqueous dispersion of organic peroxide as described herein and at least one additional cleaning product ingredient. The cleaning product may, for example, be a dishwasher detergent, a laundry detergent, a laundry bleaching product, a hard surface cleaner (e.g., a cleanser), or the like, in particular products of this type which are in liquid, cream or gel form. Suitable additional cleaning product ingredients include any of the components known to be useful in the aforementioned products, such as surfactants, carriers, bleach activators, builders, abrasives, pigments, rheology control agents, gelling agents, fragrances, anti-deposition agents, enzymes and the like.

The aforementioned products may be prepared by combining an aqueous dispersion of organic peroxide in accordance with the invention with one or more pharmaceutically acceptable ingredients, personal care ingredients or cleaning ingredients.

The organic peroxide-containing aqueous dispersions of the present invention may also be employed as polymerization initiators and hardening agents for thermoset resins and the like.

The invention may comprise various aspects, some of which may be summarized as follows.

Aspect 1: A composition, wherein the composition is an aqueous dispersion having a basic aqueous phase and comprising:
a) about 30% by weight or more of a water-insoluble, solid organic peroxide in particulate form;
b) water;
c) at least one gelling agent;
d) at least one surfactant;
e) optionally, at least one buffer; and
f) about 2% by weight or more of at least one carboxylic acid salt.

Aspect 2: The composition of Aspect 1, wherein the at least one carboxylic acid salt is comprised of a monovalent cation.

Aspect 3: The composition of Aspect 1 or 2, wherein the water-insoluble, solid organic peroxide has an average particle size of less than about 10 μm.

Aspect 4: The composition of any one of Aspects 1 to 3, wherein the at least one carboxylic acid salt includes at least one sodium or potassium salt of a carboxylic acid.

Aspect 5: The composition of any one of Aspects 1 to 4, wherein the at least one carboxylic acid salt includes at least one salt of a C2-C6 carboxylic acid comprising a monovalent cation.

Aspect 6: The composition of any one of Aspects 1 to 5, wherein the at least one carboxylic acid salt includes at least one salt of a hydroxycarboxylic acid comprising a monovalent cation.

Aspect 7: The composition of any one of Aspects 1 to 6, wherein the at least one carboxylic acid salt includes at least one of sodium lactate or potassium lactate.

Aspect 8: The composition of any one of Aspects 1 to 7, comprising from about 4 to about 12% by weight of at least one carboxylic acid salt.

Aspect 9: The composition of any one of Aspects 1 to 8, wherein the organic peroxide is benzoyl peroxide.

Aspect 10: The composition of any one of Aspects 1 to 9, wherein the at least one surfactant includes at least one nonionic surfactant.

Aspect 11: The composition of any one of Aspects 1 to 10, wherein the at least one surfactant includes at least one surfactant which is a polyglyceryl ester of one or more C6-C18 fatty acids.

Aspect 12: The composition of any one of Aspects 1 to 11, wherein the at least one gelling agent includes at least one macromolecular gelling agent.

Aspect 13: The composition of Aspect 12, wherein the at least one macromolecular gelling agent is a crosslinked macromolecular gelling agent.

Aspect 14: The composition of Aspect 12 or 13, wherein the at least one macromolecular gelling agent is crosslinked by polyvalent cations.

Aspect 15: The composition of any one of Aspects 1 to 14, wherein the at least one gelling agent includes at least one gelling agent selected from the group consisting of alginates, carrageenans, gellan gums, guar gum pectic substances, cellulose gum, microcrystalline cellulose and xanthan gums.

Aspect 16: The composition of any one of Aspects 1 to 15, wherein the basic aqueous phase has a pH of about 7.5 to 10.

Aspect 17: The composition of any one of Aspects 1 to 16, wherein the at least one carboxylic acid salt is in the aqueous phase.

Aspect 18: The composition of any one of Aspects 1 to 17, comprising from about 30 to about 50% by weight of a).

Aspect 19: The composition of any one of Aspects 1 to 18, comprising at least one buffer.

Aspect 20: The composition of any one of Aspects 1 to 19, comprising about 37 to about 42% by weight of a), about 45 to about 55% by weight of b), about 0.2 to about 2% by weight c), about 0.1 to about 2% by weight d), and about 4 to about 12% by weight f), the total of a), b), c), d) and f) being 100%.

Aspect 21: A method of decolorizing a product, comprising contacting the product with a composition in accordance with any one of Aspects 1 to 20.

Aspect 22: A pharmaceutical composition, personal care composition or cleaning product, comprising a composition in accordance with any one of Aspects 1 to 20 and at least one pharmaceutically acceptable ingredient, at least one additional personal care ingredient, or at least one additional cleaning product ingredient.

Aspect 23: A method of making a composition in accordance with any one of Aspects 1 to 20, comprising: a) mixing benzoyl peroxide having an average particle size of about 10 μm or greater, surfactant, pH adjustment agent, and water to form a first pourable dispersion; b) reducing the average particle size of the benzoyl peroxide in the first pourable dispersion to less than 10 μm, c) mixing the first pourable dispersion with a gelling agent, allowing sufficient time for the gelling agent to form a second pourable dispersion; d) mixing the second pourable dispersion with at least one carboxylic acid salt to form a third pourable dispersion; and e) optionally mixing the third pourable dispersion with at least one crosslinking agent capable of crosslinking the gelling agent.

Aspect 24: A method of making a composition in accordance with any one of Aspects 1 to 20, comprising: a) mixing benzoyl peroxide having an average particle size of 10 μm or greater, surfactant, pH adjustment agent and water to form a first pourable dispersion; b) reducing the average particle size of the benzoyl peroxide in the first pourable dispersion to less than 10 μm, c) mixing the first pourable dispersion with a pre-hydrated gelling agent to form a second pourable dispersion; d) mixing the second pourable dispersion with at least one carboxylic acid salt to form a third pourable dispersion; and e) optionally mixing the third pourable dispersion with at least one crosslinking agent capable of crosslinking the gelling agent.

Within this specification embodiments have been described in a way which enables a clear and concise specification to be written, but it is intended and will be appreciated that embodiments may be variously combined or separated without departing from the invention. For example, it will be appreciated that all preferred features described herein are applicable to all aspects of the invention described herein.

In some embodiments, the invention herein can be construed as excluding any element or process step that does not materially affect the basic and novel characteristics of the composition or process. Additionally, in some embodiments, the invention can be construed as excluding any element or process step not specified herein.

Although the invention is illustrated and described herein with reference to specific embodiments, the invention is not intended to be limited to the details shown. Rather, various modifications may be made in the details within the scope and range of equivalents of the claims and without departing from the invention.

EXAMPLES

Example 1

Formulations A-F were prepared using the ingredients listed in Table 1 (the amounts stated are in weight %) and the following procedure:

1. Mix the small particle size benzoyl peroxide, water, pH buffer and surfactant using an overhead stirrer at 1300 rpm while heating in a water bath at 35° C. Mix until well dispersed.
2. While mixing, add the glycerin, lactose, sodium lactate or magnesium sulfate. Continue mixing for an additional 10-15 minutes.
3. While mixing, add the gelling agent. Mix an additional 20-30 minutes.
4. While mixing, add the crosslinking agent. Mix for 5 minutes.

TABLE 1

| Ingredient | Formulation A Comparative | Formulation B Comparative | Formulation C Comparative | Formulation D Invention | Formulation E Invention | Formulation F Comparative |
|---|---|---|---|---|---|---|
| Benzoyl Peroxide | 40% | 40% | 40% | 40% | 40% | 40% |
| Water | >58% | >48% | >48% | >48% | >53% | >53% |
| Glycerin | — | 10% | — | — | — | — |
| Lactose | — | — | 10% | — | — | — |
| Sodium Lactate | — | — | — | 10% | 5% | — |
| MgSO$_4$ | — | — | — | — | — | 5% |
| Gelling Agent/ pH Buffer/Surfactant | <2% | <2% | <2% | <2% | <2% | <2% |

Three grams of each of Formulations A-F were weighed into separate aluminum dishes and allowed to dry at room temperature (20° C.; 68° F.). At timed intervals, each sample was weighed to determine the loss in weight. The concentration of benzoyl peroxide in each remaining sample was calculated and plotted vs. time. The results obtained are shown in FIG. 1.

Figure 2:
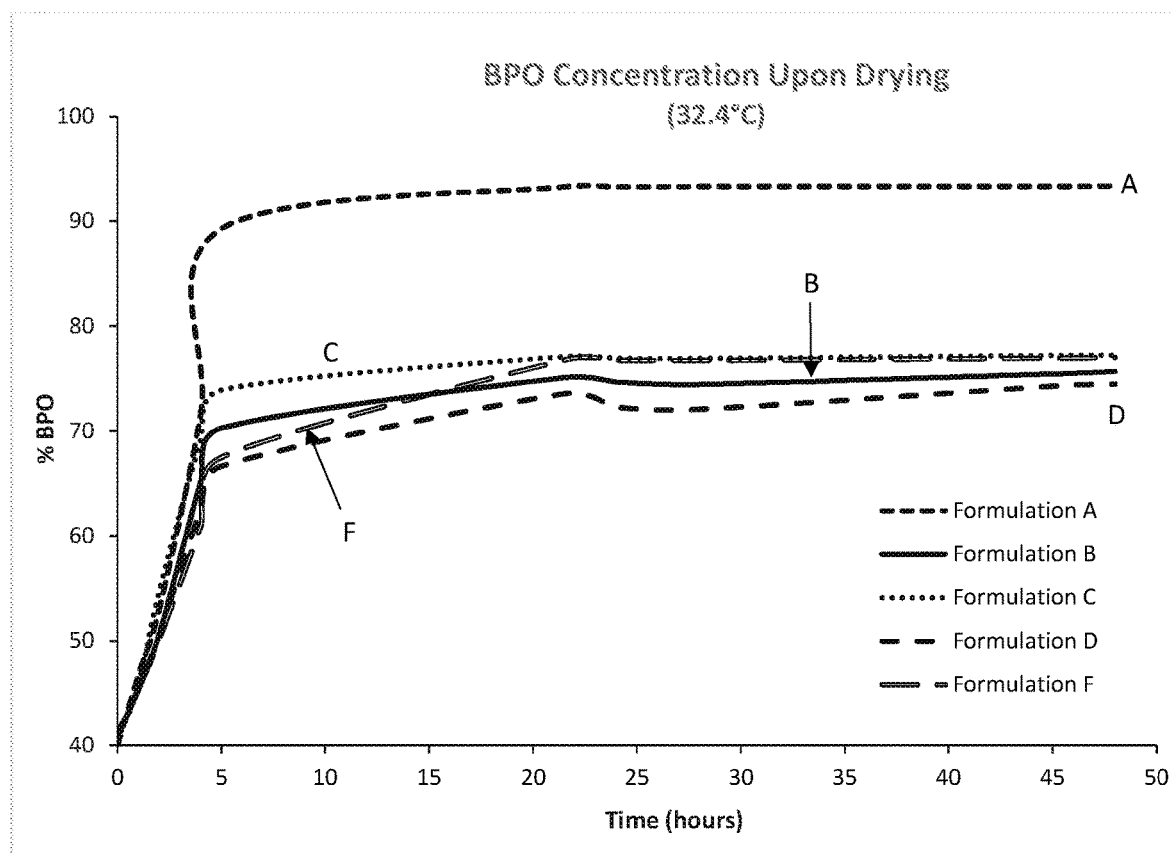

Three grams of each of Formulations A-F were weighed into separate aluminum dishes and placed in an oven set at 32.4° C. (ca. 90° F.). At timed intervals, each sample was weighed to determine the loss in weight. The concentration of benzoyl peroxide in each remaining sample was calculated and plotted vs. time. The results obtained are shown in FIG. 2.

These examples show that the addition of glycerin (Formulation B), lactose (Formulation C) or sodium lactate (Formulations D and E) slows the rate of evaporation from the aqueous dispersion both at room temperature and at an elevated temperature over an extended period of time. Sodium lactate was found to be particularly effective in slowing evaporation. The concentration of benzoyl peroxide is maintained below 90% by weight for a longer period of time as compared to the control formulation (Formulation A, which did not contain glycerin, lactose or sodium lactate), thereby providing a safer aqueous dispersion of benzoyl peroxide (i.e., one that is less susceptible to violent composition upon exposure to heat, shock or the like after being exposed to drying conditions for a period of time). Formulation D (containing 10% by weight sodium lactate) provided the best results with respect to resistance to water loss. Formulation E contained one-half as much sodium lactate as the amount of glycerin or lactose in Formulation B and Formulation C, respectively, yet exhibited a similar rate of evaporation.

Example 2

To determine the ignition properties of the aforementioned benzoyl peroxide formulations, 3.0 grams of the formulation of interest were weighed into an aluminum dish. The aluminum dish was placed in an oven set at 32.4° C. (~90° F.). At timed intervals, the sample was taken out of the oven and a flame was passed over it to determine if the material would ignite. If it ignited, the time was recorded. If the sample did not ignite, it was returned to the oven and the test was repeated until an ignition time was determined. The data below show that by adding a phlegmatizer to an aqueous dispersion of 40% benzoyl peroxide, the time to ignition upon drying is delayed as compared to a formulation without a phlegmatizer. The superior performance of sodium lactate was particularly surprising. Using sodium lactate, the same delay in ignition time can be achieved at half the loading level of other phlegmatizers (See Formulation E as compared to Formulations B, C, and F). Additionally, when the sodium lactate is tested at the same loading level as the other phlegmatizers (Formulation D), the time for ignition to occur is delayed by more than five times as compared to the standard formulation without added phlegmatizer (Formulation A).

| Formulation | Ignition Time |
| --- | --- |
| A (control) | 4.5 hours |
| B (comparative) | 8.0 hours |
| C (comparative) | 6.5 hours |
| D (invention) | 24 hours |
| E (invention) | 7.5 hours |
| F (comparative) | 6.0 hours |

Example 3

US Pressure Vessel Test: Using a stainless steel vessel with a 100 psi rupture disk and a 1.0 mm vent orifice, 5 grams of the BPO dispersion were placed in the vessel. The material was held at 50° C. for 30 minutes, after which it was heated from 50° C. to 200° C. at a rate of 0.5° C./sec. While none of the formulations ruptured the 100 psi disk, differences in the energy of the steam released upon decomposition of the BPO were observed and are recorded in the table below.

| Formulation | Characterization of the Steam Released |
| --- | --- |
| A | High Intensity - most energetic of all the samples |
| B | Low Intensity |
| C | Medium Intensity |
| E | No Steam Released |
| F | Low Intensity |

What is claimed is:

1. A composition, wherein the composition is an aqueous benzoyl peroxide dispersion which is pumpable or pourable, has a viscosity between 800 and 5000 cps, and a basic aqueous phase with a pH greater than 7 up to 10, said composition comprising:
    a) between about 30% to no more than about 50% by weight of a water-insoluble, solid benzoyl peroxide in particulate form having an average particle size of less than about 10 µm;
    b) water;
    c) at least one gelling agent, wherein the at least one gelling agent includes at least one gelling agent selected from the group consisting of alginates, carrageenans, gellan gums, guar gum pectic substances, cellulose gum, microcrystalline cellulose and xanthan gums;
    d) at least one non-ionic surfactant;
    e) optionally, at least one buffer; and
    f) at least 2% by weight or more of at least one carboxylic acid salt including at least one of sodium lactate or potassium lactate, such that said carboxylic acid salt is present in an amount effective to reduce water evaporation or the rate at which water evaporates from the aqueous dispersion;
    the total of a), b), c), d) and f) being 100%.

2. The composition of claim 1, comprising from about 4 to about 12% by weight of the at least one carboxylic acid salt.

3. The composition of claim 1, wherein the at least one surfactant includes at least one surfactant which is a polyglyceryl ester of one or more C6-C18 fatty acids.

4. The composition of claim 1, wherein the at least one gelling agent is crosslinked.

5. The composition of claim 1, wherein the basic aqueous phase has a pH of 7.5 to 10.

6. The composition of claim 1, wherein the at least one carboxylic acid salt is in the aqueous phase.

7. The composition of claim 1, comprising at least one buffer.

8. The composition of claim 1, comprising about 37 to about 42% by weight of a), about 45 to about 55% by weight of b), about 0.2 to about 2% by weight c), about 0.1 to about 2% by weight d), and about 4 to about 12% by weight f), the total of a), b), c), d) and f) being 100%.

9. A method of decolorizing a product, comprising contacting the product with a composition in accordance with claim 1.

10. A pharmaceutical composition, personal care composition or cleaning product, comprising a composition in accordance with claim 1 and at least one pharmaceutically acceptable ingredient, at least one additional personal care ingredient, or at least one additional cleaning product ingredient.

11. A method of making a composition in accordance with claim 1, comprising: a) mixing benzoyl peroxide having an average particle size of about 10 µm or greater, surfactant, pH adjustment agent, and water to form a first pourable dispersion; b) reducing the average particle size of the benzoyl peroxide in the first pourable dispersion to less than 10 µm, c) after steps a) and b) mixing the first pourable dispersion with said gelling agent, allowing sufficient time for the gelling agent to form a second pourable dispersion; d) mixing the second pourable dispersion with at least one carboxylic acid salt including at least one of sodium lactate or potassium lactate to form a third pourable dispersion; and e) optionally mixing the third pourable dispersion with at least one crosslinking agent capable of crosslinking the gelling agent.

12. A method of making a composition in accordance with claim 1, comprising: a) mixing benzoyl peroxide having an average particle size of 10 µm or greater, surfactant, pH adjustment agent and water to form a first pourable dispersion; b) reducing the average particle size of the benzoyl peroxide in the first pourable dispersion to less than 10 µm, c) after steps a) and b) mixing the first pourable dispersion with said gelling agent which is prehydrated to form a second pourable dispersion; d) mixing the second pourable dispersion with at least one carboxylic acid salt including at least one of sodium lactate or potassium lactate to form a third pourable dispersion; and e) optionally mixing the third pourable dispersion with at least one crosslinking agent capable of crosslinking the gelling agent.

13. The composition of claim 1 comprising at least 3% by weight of at least one of sodium lactate or potassium lactate.

* * * * *